United States Patent [19]

Tsuda et al.

[11] Patent Number: 4,644,012
[45] Date of Patent: Feb. 17, 1987

[54] TREATMENT FOR OSTEOPOROSIS

[75] Inventors: Masao Tsuda, Hyogo; Yoichi Sawa, Sengokuhigashi; Iwao Yamazaki, Hyogo, all of Japan

[73] Assignee: Takeda Chemical Industries, Ltd., Osaka, Japan

[21] Appl. No.: 684,144

[22] Filed: Dec. 20, 1984

[30] Foreign Application Priority Data

Dec. 21, 1983 [JP] Japan .................................. 58-242779
Dec. 21, 1983 [JP] Japan .................................. 58-242780

[51] Int. Cl.⁴ .............................................. A61K 31/35
[52] U.S. Cl. ..................... 514/456; 514/320; 514/255; 514/234; 549/403
[58] Field of Search ............... 514/456, 234, 255, 320; 549/403

[56] References Cited

U.S. PATENT DOCUMENTS 3,864,362  2/1975  Feuer et al. ........................ 549/403
3,907,830  9/1975  Feuer et al. ........................ 549/403
4,163,746  8/1979  Feuer et al. ........................ 549/403

FOREIGN PATENT DOCUMENTS 953978  4/1964  United Kingdom .

OTHER PUBLICATIONS

Central Patents Index B-FARMADOC 54701T-B, B2, Sako, 20-07-70, Week T34, Oct. 13, 1972, 53371T-55066T.
Central Patent Index B-FARMADOC 23421V/13, *FR2190-411, Week V13, May 20, 1974, 22836V-24842V.

Primary Examiner—Nicky Chan
Attorney, Agent, or Firm—Wegner & Bretschneider

[57] ABSTRACT

A compound of the formula

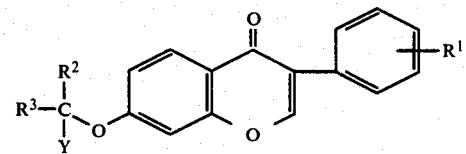

wherein $R^1$ is hydrogen or hydroxy, $R^2$ and $R^3$ are independently hydrogen or lower alkyl and Y is carboxyl or a group convertible to carboxyl is effective for prevention or treatment of osteoporosis.

10 Claims, No Drawings

TREATMENT FOR OSTEOPOROSIS

This invention relates to a pharmaceutical preparation for prevention or treatment of osteoporosis which contains, as an active ingredient, a 3-phenyl-4H-1-benzopyran-4-one derivative of the formula

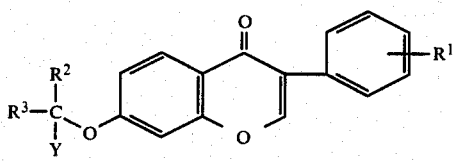

wherein $R^1$ is hydrogen or hydroxy, $R^2$ and $R^3$ are independently hydrogen or lower alkyl and Y is carboxyl or a group convertible to carboxyl.

Osteoporosis is a disease condition or illness wherein the quantitative loss of bones has progressed beyond a certain limit causing some symptoms or risk manifestations. It is seen most commonly in the elderly. Among its main clinical manifestations are kyphosis, low back pain, and fractures of femoral neck, lower end of the radius, ribs, upper end of the humerus, etc. The pathogenic factors are varied, including endocrine disorder and nutritional disorder. There are therapeutic agents such as estrogen preparations, calcitonin, vitamin D, calcium preparations, but these are either limited in effect to a given subject or only of indefinite effect.

Therefore, the present inventors studied more general drugs which inhibit resorption of bones by their direct action on bone. As a result, the inventors have found that a 3-phenyl-4H-1-benzopyran-4-one derivative of the formula [I] exhibits a sufficient inhibitory action on bone resorption by its direct action on bone. These compounds are of the formula

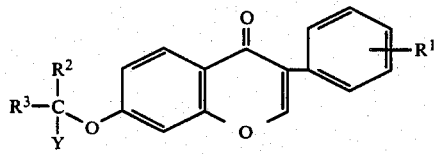

wherein each of the symbols is as defined hereinbefore.

The object of the present invention is to provide a pharmaceutical preparation for prevention or treatment of osteoporosis which contains a 3-phenyl-4H-1-benzopyran-4-one derivative of the formula [I] (hereinafter sometimes referred to as "the compound [I]")as an active ingredient.

When $R^1$ in the formula [I] is hydroxy, it may be present in any position of the phenyl ring. $R^2$ and $R^3$ are independently hydrogen or lower alkyl. As said lower alkyl, there may be mentioned methyl, ethyl, propyl, and butyl, etc. The group Y, which is convertible to carboxyl, is, for example, an esterified carboxyl group or an amidated carboxyl group. Examples of the former are alkoxycarbonyl (e.g. methoxycarbonyl, ethoxycarbonyl, propoxycarbonyl, butoxycarbonyl), aralkoxycarbonyl (e.g. benzyloxycarbonyl) and aryloxycarbonyl (e.g. phenyloxycarbonyl). The latter includes, among others, carbamoyl, N-methylcarbamoyl, N-ethylcarbamoyl, N,N-dimethylcarbamoyl, N,N-diethylcarbomoyl, N-morpholinocarbonyl, N-piperidinocarbonyl or N-piperazinocarbonyl.

When Y in the formula [I] is carboxyl, that is when the compound [I] is of the carboxylic acid type, it may be used in the form of sodium salt, potassium salt, calcium salt, etc.

Especially preferred are novel compounds of formula (I) wherein Y is COOH, $R^1$ is hydrogen or hydroxy, $R^2$ is lower alkyl of one to four carbon atoms and $R^3$ is hydrogen.

Of the compound [I] of the present invention, some are known compounds and known to have anticonvulsant activity, muscular relaxant activity, cardioactive property, vascular tissue resistance-increasing activity (Japanese Patent Publication No. 32074/1972), coronary vasodilating activity (British Patent No. 953978), etc., but it has been unknown that any of the compounds is useful for the treatment of osteoporosis.

The compound [I] can be produced, for example, by reacting a hydroxy compound of the formula [II] with an α-halocarboxylic acid or a derivative thereof of the formula [III], if necessary followed by hydrolysis.

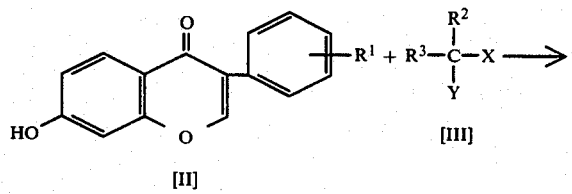

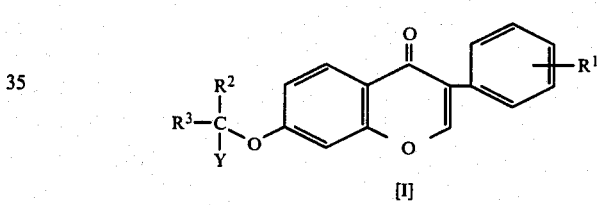

In the above formulas, X is halogen, and $R^1$, $R^2$, $R^3$ and Y are as defined hereinbefore.

The starting compound [II] which is employed in the present invention can be prepared, for example, by the method of E. M. Gaydou et al. (Bull. Soc. Chim. Fr., 1978, II-43) or the method of S. A. Kagal et al. (Tetrahedron Letters, 1962, 593). The α-halocarboxylic acid derivative of the formula [III] includes esters, amides, etc., and the compound of the formula [III] includes, among others, 2-chloropropionic acid, 2-bromobutyric acid, 2-iodovaleric acid, 2-bromocaproic acid, methyl chloroacetate, methyl 2-chloropropionate, methyl 2-bromobutyrate, ethyl 2-chloropropionate, ethyl 2-bromovalerate, propyl 2-chloropropionate, propyl 2-bromocaproate, butyl 2-chloropropionate, butyl 2-bromopropionate, methyl 2-iodoheptanoate, chloroacetamide, bromoacetic acid ethylamide, chloroacetic acid dimethylamide, bromoacetic acid morpholide, chloroacetic acid piperidide, bromoacetic acid piperidide, 2-chloropropionamide, and 2-bromobutyric acid diethylamide.

Among the compounds according to the present invention, those wherein Y in the formula [I] is an amidated carboxyl group can also be prepared, for example, by reacting a 7-oxyacetic acid ester derivative of 3-phenyl-4H-1-benzopyran-4-one, represented by the formula [I], with ammonia or an amine. As said amine, there may be mentioned, for example, methylamine, ethylamine, dimethylamine, diethylamine, piperidine, morpholine, piperazine, etc.

Generally, the condensation reaction described above is advantageously carried out in the presence of an inert solvent. As such solvent, there may be used any solvent which will not interfere with said reaction. Such solvent may suitably be selected, for instance, from among alcohols (e.g. methanol, ethanol, propanol, isopropyl alcohol, butanol), ketones (e.g. acetone, methyl isobutyl ketone, cyclohexanone), ethers (e.g. tetrahydrofuran, dioxane, diethyl ether, isopropyl ether), halogenated hydrocarbons (e.g. dichloromethane, dichloroethane, chloroform), petroleum ether, toluene, xylene, dimethylformamide, pyridine, aldehyde collidine, water, and mixed solvents composed of two or more of these.

The above condensation reaction is advantageously carried out in the presence of a deacidifying agent, such as an alkali metal hydrogen carbonate (e.g. sodium hydrogen carbonate, potassium hydrogen carbonate), an alkali metal hydroxide (e.g. sodium hydroxide, potassium hydroxide), an alkali metal carbonate (e.g. sodium carbonate, potassium carbonate), sodium amide, sodium hydride, an alkali metal (e.g. sodium, potassium), a sodium alcoholate (e.g. sodium methylate, sodium ethylate), or an organic base (e.g. pyridine, aldehyde collidine, dimethylaniline, triethylamine).

Hydrolysis of the compound of the formula [I] in which Y is an esterified carboxyl group or an amidated carboxyl group is carried out in the conventional manner. Thus, the hydrolysis is conducted in the presence of a catalyst usable in generally known hydrolysis reactions. Said catalyst is, for instance, an inorganic acid (e.g. sulfuric acid, hydrochloric acid, hydrobromic acid), an organic acid [e.g. toluenesulfonic acid, benzenesulfonic acid, strongly acidic ion exchange resin (e.g. Amberlite IR-120)], or a mixture thereof.

Referring to the above formula [III], the halogen atom represented by X includes chlorine, bromine, iodine, or fluorine, whereas the lower alkyl group represented by R includes those containing 1 to 4 carbon atoms, such as methyl, ethyl, propyl, isopropyl, butyl, isobutyl, secondary butyl and tertiary butyl.

The reaction temperature, solvent and other reaction conditions may be selected in an adequate manner depending on each specific case.

The thus-produced compound [I] of the present invention can be isolated from the reaction mixture and purified by conventional methods of treatment (e.g. extraction, recrystallization, chromatography).

The following experimental examples show that the compound [I] has bone resorption inhibiting activity which is effective for the treatment of osteoporosis.

TEST EXAMPLE 1

Bone resorption inhibiting activity of 7-(1-hydroxycarbonylethyl)oxy-3-phenyl-4H-1-benzopyran-4-one (hereinafter referred to as "compound A") in rat fetal long bone culture Determination of bone resorption was performed by the method of Raisz [J. Clin. Invest. 44, 103–116 (1965)]. Thus, a Sprague-Dawley rat on the 19th day of pregnancy was subcutaneously injected with 50μ Ci of $^{45}Ca$ (isotope of calcium, $CaCl_2$ solution), and was laparotomized on the following day. The embryos were aseptically taken out, the forelimbs (radius and ulna) were cut off from the trunk under a binocular dissecting microscope, and the connective tissue and cartilage were removed as much as possible to prepare bone samples. Each bone sample was preincubated at 37° C. for 24 hours in 0.6 ml of the medium containing 2 mg/ml of bovine serum albumin in $BGJ_b$ medium (Fitton-Jackson modification) [GIBCO Laboratories, Grand Island, N.Y. 14072 U.S.A.]. Then, the sample was further incubated for 3 days in the same medium as above in which 10 μg/ml of compound A had been incorporated. Then, the radioactivity of $^{45}Ca$ in the medium and that of $^{45}Ca$ in the bone were measured and the percentage (%) of $^{45}Ca$ released from the bone into the medium was calculated by the following formula.

Percentage (%) of $^{45}Ca$ released from bone into medium =

$$\frac{\text{Count of }^{45}\text{Ca in medium}}{\text{Count of }^{45}\text{Ca in medium} + \text{Count of }^{45}\text{Ca in bone}} \times 100$$

As control, the bones of the embryos from the same litter were similarly incubated in the absence of compound A for 3 days. The mean ± standard deviation for the six bones per group are shown in Table 1. It is apparent that compound A suppressed bone resorption.

TABLE 1

| | Concentration of compound A | $^{45}$Ca (%) released |
|---|---|---|
| Control group | 0 | 23.6 ± 3.9 |
| Test group | 10 μg/ml | 18.5 ± 2.2* |

*A significant difference from the control group ($p < 0.05$)

TEST EXAMPLE 2

Potentiating effect of 7-(1-hydroxycarbonylethyl)-oxy-3-(4-hydroxyphenyl)-4H-1-benzopyran-4-one (hereinafter referred to as "compound B") and 7-(1-ethoxycarbonylethyl)-oxy-3-phenyl-4H-1-benzopyran-4-one (hereinafter referred to as "compound C") on the bone resorption inhibiting action of calcitonin in rat fetal long bone culture The bone samples prepared in the same manner as Test Example 1 were preincubated for 24 hours in the same medium as that prepared in Test Example 1, which contains bovine serum albumin in $BGJ_b$ medium (Fitton-Jackson modification). Then, in the concomitant presence of PTH (parathyroid hormone, a bone resorption stimulant), calcitonin and compound B or compound C, the samples were further incubated for 3 days and the percentage of $^{45}Ca$ released into the medium was calculated by means of the same formula as that in Test Example 1. The results are shown in Table 2. As control experiments, the same determination was made for a control I group using the medium supplemented with PTH alone and a control II group using the medium supplemented with PTH and calcitonin. It is apparent from Table 2 that compound B and compound C potentiated the inhibitory action of calcitonin on PTH-stimulated bone resorption.

TABLE 2

| | Concentration of calcitonin | Concentration of compound | $^{454}$Ca (%) released |
|---|---|---|---|
| Control I group | 0 | 0 | 39.7 ± 1.5 |
| Control II group | 3 mU/ml | 0 | 35.9 ± 4.9 |
| Test group I | 3 mU/ml | Compound B 25 μg/ml | 31.2 ± 3.4 |
| Test group II | 3 mU/ml | Compound C 25 μg/ml | 32.2 ± 2.7 |

TEST EXAMPLE 3

Acute toxicity

Five-week-old ICR mice and 5-week-old Sprague-Dawley rats were used in groups of 10 males and 10 females, and suspensions of compound A or compound B in olive oil were administered orally [2,500, 5,000 and 10,000 mg/kg of each compound] or subcutaneously [1,250, 2,500 and 5,000 mg/kg]. The animals were kept under observation for 14 days. None of the groups showed deaths, nor toxic symptoms, which might be attributable to compound A or B, with the result that $LD_{50}$ could not be calculated.

When the compound [I] of this invention is used for the treatment of osteoporosis, it is orally administered in a usual daily dose of about 10 to 500 mg for an adult human, in such dosage forms as tablets, powders, granules, capsules, liquids, etc. or parenterally administered as, for example, injections at a dose level of about 1 to about 100 mg per injection for an adult human.

EXPERIMENTAL EXAMPLE 1

A mixture of 40 g of 7-hydroxy-3-phenyl-4H-1-benzopyran-4-one, 46 g of ethyl 2-bromopropionate, 250 ml of dimethylformamide and 46.5 g of potassium carbonate was stirred well with heating at 80° C. for 2 hours and poured into 270 ml of ice water. The resulting crystalline precipitate was collected by filtration and recrystallized from ethyl acetate-ethanol to give 103 g of 7-(1-ethoxycarbonylethyl)oxy-3-phenyl-4H-1-benzopyran-4-one as white crystals. m.p. 165°–166° C.

Elemental Analysis. Calcd. for $C_{20}H_{18}O_5$: C, 71.00; H, 5.36. Found: C, 71.19; H, 5.41.

EXPERIMENTAL EXAMPLE 2

A mixture of 4.0 g of 7-hydroxy-3-(4-hydroxyphenyl)-4H-1-benzopyran-4-one, 3.42 g of ethyl 2-bromopropionate, 60 ml of dimethylformamide and 4.3 g of potassium carbonate was stirred well with heating at 80° C. for 2 hours, poured into ice water and extracted with ethyl acetate. The extract was washed with water and concentrated and the residue was recrystallized from dichloroethane to give 3.0 g of 7-(1-ethoxycarbonylethyl)oxy-3-(4-hydroxyphenyl)-4H-1-benzopyran-4-one as white crystals. m.p. 172°–173° C.

Elemental Analysis. Calcd. for $C_{20}H_{18}O_6$: C, 67.79; H, 5.12. Found: C, 67.72; H, 5.18.

In the same manner as above, the following compounds were obtained.

7-(1-Ethoxycarbonylethyl)oxy-3-(3-hydroxyphenyl)-4H-1-benzopyran-4-one. m.p. 193°–194° C.

Elemental analysis. Calcd. for $C_{20}H_{18}O_6$: C, 67.79; H, 5.12. Found: C, 67.61; H, 5.28.

7-(1-Ethoxycarbonylethyl)oxy-3-(2-hydroxyphenyl)-4H-1-benzopyran-4-one. m.p. 154°–156° C.

NMR (DMSO-$d_6$)δ:1.25(3H, t, $CH_3$), 1.60(3H, d, $CH_3$), 4.20(2H, q, $CH_2$), 5.25(1H, q, CH), 6.8–7.4(6H, m, aromatic H), 8.05(1H, d, $C_5$—H), 8.25(1H, s, $C_2$13 H), 9.30(1H, bs, OH).

EXPERIMENTAL EXAMPLE 3

A mixture of 20 g of 7-(1-ethoxycarbonylethyl)oxy-3-phenyl-4H-1-benzopyran-4-one, 200 ml of dioxane, 70 ml of hydrochloric acid and 150 ml of water was refluxed for 4 hours and poured into ice water. The resulting crystalline precipitate was collected by filtration and recrystallized from ethanol to give 17.1 g of 7-(1-hydroxycarbonylethyl)oxy-3-phenyl-4H-1-benzopyran-4-one as white crystals. m.p. 223° C.

Elemental Analysis. Calcd. for $C_{18}H_{14}O_5$: C, 69.67; H, 4.55. Found: C, 69.68; H, 4.52.

Using 7-(1-ethoxycarbonylethyl)oxy-3-(4-hydroxyphenyl)-4H-1-benzopyran-4-one and following the same procedure as above, 7-(1-hydroxycarbonylethyl)oxy-3-(4-hydroxyphenyl)-4H-1-benzopyran-4-one was obtained as white crystals. m.p. 201°–202° C.

NMR (DMSO-$d_6$)δ:1.57(3H, d, $CH_3$), 5.07(1H, q, CH), 6.83(2H, d, aromatic H), 6.95–7.20(2 H, m $C_6$ and $C_8$—H), 8.04(1H, d, $C_5$—H), 8.31(1H, s, $C_2$—H).

EXPERIMENTAL EXAMPLE 4

A mixture of 3.0 g of 7-(1-ethoxycarbonylethyl)oxy-3-(3-hydroxyphenyl)-4H-1-benzopyran-4-one, 90 ml of dioxane, 120 ml of water and 15 ml of hydrochloric acid was refluxed for 2.5 hours, poured into ice water and extracted with ethyl acetate. The extract was washed with water and concentrated and the residue was recrystallized from ethyl acetate-dichloroethane to give 2.5 g of 7-(1-hydroxycarbonylethyl)oxy-3-(3- hydroxyphenyl)-4H-1-benzopyran-4-one as white crystals. m.p. 218°–219° C.

Elemental Analysis. Calcd. for $C_{18}H_{14}O_6 \cdot \frac{1}{4}H_2O$: C, 65.34; H, 4.72. Found: C, 65.31; H, 4.54.

Using 7-(1-ethoxycarbonylethyl)oxy-3-(2-hydroxyphenyl)-4H-1-benzopyran-4-one and following the same procedure as above, the following compound was obtained.

7-(1-Hydroxycarbonylethyl)oxy-3-(2-hydroxyphenyl)-4H-1-benzopyran-4-one. m.p. 180°–182° C.

NMR (DMSO-$d_6$)δ:1.55 (3H, d, $CH_3$), 5.10(1H, q, CH), 6.6–7.4(6H, m, aromatic H), 8.05(1H, d, $C_5$—H), 8.20 (1H, s, $C_2$—H), 9.3 (1H, bs, OH).

Example 1 Tablets

| | | |
|---|---|---|
| (I) 7-(1-Hydroxycarbonylethyl)-oxy-3-phenyl-4H—1-benzopyran-4-one | | 200 g |
| (II) Lactose | | 15 g |
| (III) Starch | | 45 g |
| (IV) Carboxymethylcellulose calcium | | 10 g |
| (V) Magnesium stearate | | 1 g |

The above components (I) through (V) were admixed to prepare 1000 uncoated tablets with a diameter of 8.5 mm.

Example 1 Capsules

| | | |
|---|---|---|
| (I) 7-(1-Hydroxycarbonylethyl)-oxy-3-(4-hydroxyphenyl)-4H—1-benzopyran-4-one | | 200 g |
| (II) Lactose | | 40 g |
| (III) Starch | | 50 g |
| (IV) Hydroxypropylcellulose | | 7 g |
| (V) Magnesium stearate | | 3 g |

The above components (I) through (V) were admixed and filled into 1000 No. 1 capsules.

What is claimed is:

1. A method for prevention or treatment of osteoporosis, which comprises administering to a patient in need of such prevention or treatment, as an active ingredient, an effective amount of a compound of the formula

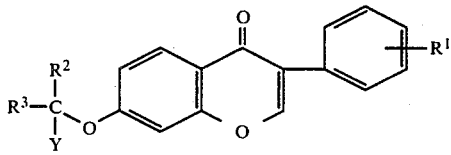

wherein R¹ is hydrogen or hydroxy, R² and R³ are independently hydrogen or lower alkyl and Y is carboxyl, (C₁₋₄-alkoxy)carbonyl, benzyloxy-carbonyl, phenyloxycarbonyl, carbamoyl, N-methylcarbamoyl, N-ethycarbamoyl, N,N-dimethylcarbamoyl, N,N-diethylcarbamoyl, N-morpholinocarbonyl, N-piperidinocarbonyl or N-piperazinocarbonyl.

2. A method for prevention or treatment of osteoporosis, which comprises administering to a patient in need of such prevention or treatment, as an active ingredient, an effective amount of a compound of the formula

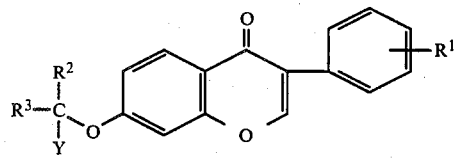

wherein R¹ is hydrogen or hydroxy, R² and R³ are independently hydrogen or lower alkyl and Y is carboxyl or C₁₋₄-(alkoxy)carbonyl.

3. A method for prevention or treatment of osteoporosis of claim 1, which comprises administering to a patient in need of such prevention or treatment, as an active ingredient, an effective amount of a compound of the formula

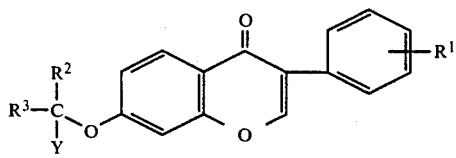

wherein R¹ is hydrogen or hydroxy, R² is hydroqen, R³ is lower alkyl and Y is carboxyl or lower alkoxycarbonyl.

4. A method of claim 1, wherein the compound to be administered is 7-(1-hydroxycarbonylethyl) oxy-3-phenyl-4H-1-benzopyran-4-one.

5. A method of claim 1, wherein the compound to be administered is 7-(1-hydroxycarbonylethyl) oxy-3-(4-hydroxyphenyl)-4H-1-benzopyran-4-one.

6. A method of claim 1, wherein the compound to be administered is 7-(1-ethoxycarbonylethyl) oxy-3-phenyl-4H-1-benzopyran-4-one.

7. A method of claim 1, wherein the compound to be administered is 7-(1-ethoxycarbonylethyl) oxy-3-(4-hydroxyphenyl)-4H-1-benzopyran-4-one.

8. A method of claim 1, wherein the patient in need of such prevention or treatment is elderly.

9. A method of claim 1, wherein administration of the compound is conducted orally in a daily dose of from about 10 to about 500 mg for an adult human.

10. A method of claim 1, wherein administration of the compound is conducted parenterally in a dose level of about 1 to about 100 mg per injection for an adult human.

* * * * *